United States Patent [19]

Iwakiri

[11] Patent Number: Plant 6,075

[45] Date of Patent: Jan. 5, 1988

[54] ASIAN PEAR TREE NAMED DAISUI LI

[75] Inventor: Ben T. Iwakiri, Sacramento, Calif.

[73] Assignee: The Regents of the University of California, Berkeley, Calif.

[21] Appl. No.: 814,113

[22] Filed: Dec. 27, 1985

[51] Int. Cl.[4] ..... A01H 5/03

[52] U.S. Cl. ..... Plt./36

[58] Field of Search ..... Plt. 36

*Primary Examiner*—Robert E. Bagwill

*Attorney, Agent, or Firm*—Townsend and Townsend

[57] ABSTRACT

An Asian pear tree which is of large to medium size, vigorous, upright to slightly spreading, tall, open, medium growing and hardy; foliated with large, wide, long, medium thick, leathery, ovate leaves having acuminate apices, a margin with sharply setose serration, and a petiole of medium length and thickness; blooms early with white, medium size, fertile flowers; and is a regular and productive bearer of large to very large, obovate to globular fruit having skin which is smooth, thick to medium thick, and medium green to light green at maturity, and white flesh which is firm, somewhat coarse, crisp, tender, juicy, sweet, and subacid with a trace of tartness.

1 Drawing Figure

BACKGROUND OF THE VARIETY

Field of the Invention

In the conduct of an extensive plant breeding program, I originated a substantial number of new and distinct varieties of fruit trees, and which included the herein-claimed variety of Asian pear tree; such plant breeding program having been undertaken by me at the University of California, Davis, Yolo County, Calif., in its research nursery, and in one of its experimental orchards.

CLASSIFICATION OF THE VARIETY

The present variety of Asian pear tree (identified by test selection number "12-44") is embraced by Class 36, Plants, of the U.S. Patent Office Manual of Classification.

PRIOR VARIETIES

Among existing varieties which are known to me, and mentioned herein, are the Asian pears Kikusui, Tsu Li, Ya Li, Shinko, and Chojuro; and the domestic Bartlett.

ORIGIN OF THE VARIETY

The present variety of Asian pear tree was originated by me in the aforesaid experimental nursery and orchard as a cross between the Kikusui and Tsu Li varieties of Asian pears. A substantial number of the resulting seeds were initially grown in a greenhouse, then in the nursery, and later transplanted to an experimental orchard near Winters, Calif., where such seedlings were maintained under close and continuing observation. Upon bearing fruit, one of such seedlings evidenced certain novel and distinctive characteristics and was selected for asexual reproduction, with a view toward possible ultimate commercial introduction.

ASEXUAL REPRODUCTION OF THE VARIETY

Subsequent to its origination and selection, as above, the herein-claimed variety of Asian pear tree was asexually reproduced by me by top-grafting on compatible pear seedlings in the aforesaid experimental orchard and, in maturity, the reproductions ran true to the original tree in all respects.

SUMMARY OF THE VARIETY

The herein-claimed variety of Asian pear tree is of large to medium size, vigorous, upright to slightly spreading, tall, open, medium growing, and hardy; foliated with large, wide, long, medium thick, leathery, ovate leaves having acuminate apices, a margin with sharply setose serration, and a petiole of medium length and thickness; blooms early with white, medium size, fertile flowers; and is a regular and productive bearer of large to very large, obovate to globular fruit having skin which is smooth, thick to medium thick, and medium green to light green at maturity, and white flesh which is firm, somewhat coarse, crisp, tender, juicy, sweet and subacid with a trace of tartness.

The herein-claimed variety of Asian pear tree is further, and more particularly, characterized by a tree which is compatible with all pear rootstocks and grows more vigorously on them than other Asian pear varieties; blooms slightly after the Ya Li and Tsu Li and more nearly with the Chojuro and Kikusui, but earlier than the Bartlett; and by the regular and productive bearing of large to very large fruit (which minimizes thinning) which becomes picking and eating ripe after the Bartlett and the Shinko; the fruit being more pear-shaped than most Asian pear varieties, including Asian pear selection "12-43" which is the subject of my U.S. plant patent application Ser. No. 06/814,248 filed 12/27/85. Additionally, the fruit—of excellent quality—has a smooth, clean appearance, and the white flesh (soluble solids 14%) is refreshingly mild; the fruit having a storage life of five to six months at 32° F.

BRIEF DESCRIPTION OF THE DRAWING

The drawing is an illustration, by photographic reproduction in color, of separate fruit of the variety; certain of the fruit being shown whole, while other fruit is half cut-away to expose the flesh.

DESCRIPTION OF THE VARIETY

The botanical details of the present new and distinct variety of Asian pear tree—with color definitions in common color terms—are as follows:

Tree:
- *Size.*—Large to medium.
- *Vigor.*—Vigorous.
- *Growth.*—Upright. Slightly spreading. Tall. Open. Medium growth rate.
- *Hardiness.*—Hardy.
- *Production.*—Productive.
- *Bearing.*—Regular bearer.

Trunk:
- *Size.*—Medium.
- *Texture.*—Medium. Craggy.

Branches:
- *Size.*—Medium.
- *Texture.*—Smooth.
- *Color.*—Brown undercolor, overlaid with a grayish white scarf skin.
- *Lenticels.*—Number: Numerous. Size: Large. Texture: Raised. Rough.

Leaves:
- *Size.*—Large. Long — Average length — 14 cm. Wide — Average width — 9 cm.
- *Texture.*—Smooth.
- *Form.*—Ovate. Apices acuminate.
- *Thickness.*—Medium. Leathery.
- *Color.*—top side — Dark green. Under side — Light green.
- *Margin.*—Sharply setose serration.
- *Petiole.*—Medium length — Average — 3.5 cm. Medium thickness.

Flowers:
- *Date of bloom.*—Early — Usually 3rd week in March.
- *Size.*—Medium.
- *Color.*—White.
- *Fertility.*—Fertile.

Fruit:
- *Date of ripening.*—Usually first three weeks of September (at about flesh firmness of 10 lbs., and when skin color turns from dark green to medium to light green.).
- *Tenacity.*—Hangs well on tree.
- *Size.*—Large to very large (12–16 oz. when ripe). Average length — 80 mm. Average width — 89 mm.
- *Form.*—Slightly variable. Obovate to globular. Slightly irregular.
- *Stem.*—Medium length — average — 3.6 mm.
- *Cavity.*—Acute. Medium depth. Medium breadth. Slightly russeted. Furrowed. Angular. Some lipped.
- *Calyx.*—May be deciduous, partly persistent or persistent. When calyx partly persistent: Open, medium size. When calyx deciduous: Scarred area where sepals were attached are light brown and scaly.
- *Lobes.*—When calyx persistent: Separated at base, erect, connivent, medium length, medium width, acute.
- *Basin.*—When calyx persistent: Medium depth, medium width, surface smooth, furrowed, angular. When calyx deciduous: Deep, wide, sides sloping, furrowed and angular, surface smooth.

Skin:
- *Thickness.*—Thick to medium.
- *Texture.*—Smooth. Some may have patches of russet. Dull.
- *Color.*—Dark green turning to medium to light green as fruit matures.
- *Dots.*—Numerous. Large to medium. Russet. Raised.

Flesh:
- *Color.*—White.
- *Texture.*—Firm. Somewhat coarse. Crisp. Tender. Juicy.
- *Flavor.*—Sweet. Subacid. Trace of tartness.
- *Aroma.*—Distinct. Similar to Tsu Li.
- *Quality.*—Best.

Core:
- *Size.*—Medium to small. Open. Abaxile.

Core lines:
- *form.*—Clasping.

Calyx tube:
- *Length.*—Medium.
- *Width.*—Medium.
- *Form.*—Urn-shaped.

Seed:
- *Size.*—Medium.
- *Form.*—Plump.
- *Shape.*—Acute-Acuminate.

Use: Dessert. Kitchen. Market. Home.

Keeping quality: Good. Long storage life (five to six months at 32° F.).

Resistance to insects: Equivalent to other Asian pear varieties, and the Bartlett.

Resistance to disease: Equivalent to other Asian pear varieties.

Shipping quality: Good.

The Asian pear tree and its fruit herein described may vary in slight detail due to climatic and soil conditions under which the variety may be grown; the present description being of the variety as grown in the Sacramento Valley of California.

I claim:

1. A new and distinct variety of Asian pear tree, substantially as illustrated and described, characteristically including—in comparison to other Asian pear varieties—the regular and productive bearing of large to very large fruit which becomes picking and eating ripe after the Bartlett and the Shinko; the fruit, of excellent quality, being smooth and clean in appearance, and the flesh being white, firm, tender, crispy, juicy, sweet with a faint trace of tartness, and refreshingly mild; the storage life of the fruit being five to six months at 32° F.

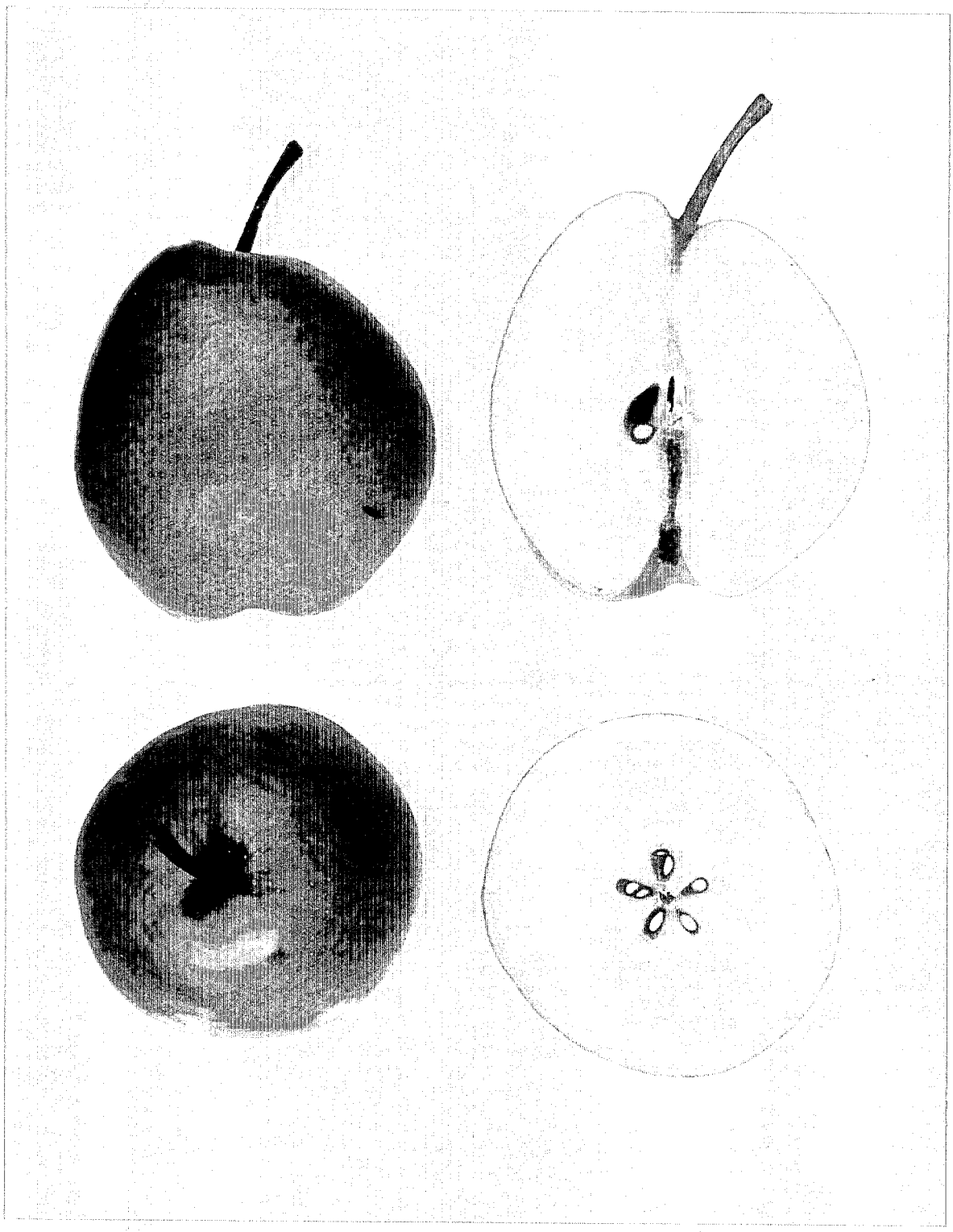

* * * * *